US00PP19346P2

(12) United States Plant Patent
Koppe

(10) Patent No.: US PP19,346 P2
(45) Date of Patent: Oct. 21, 2008

(54) ***BEGONIA* PLANT NAMED 'ELEKTRA WHITE'**

(50) Latin Name: *Begonia×hiemalis*
Varietal Denomination: Elektra White

(75) Inventor: Lubbertus H. Koppe, Putten (NL)

(73) Assignee: Koppe Royalty B.V., Ermelo (NL)

( * ) Notice: Subject to any disclaimer, the term of this patent is extended or adjusted under 35 U.S.C. 154(b) by 0 days.

(21) Appl. No.: 11/978,114

(22) Filed: Oct. 25, 2007

(51) Int. Cl.
*A01H 5/00* (2006.01)

(52) U.S. Cl. ..... Plt./345
(58) Field of Classification Search ..... Plt./345
See application file for complete search history.

*Primary Examiner*—Annette H Para
(74) *Attorney, Agent, or Firm*—C. A. Whealy

(57) ABSTRACT

A new and distinct cultivar of *Begonia* plant named 'Elektra White', characterized by its upright and mounded plant habit; freely branching habit; double flowers that are white in color and held above and beyond the foliage; and excellent postproduction longevity.

1 Drawing Sheet

Botanical designation: *Begonia×hiemalis.*
Cultivar denomination: 'ELEKTRA WHITE'.

BACKGROUND OF THE INVENTION

The present invention relates to a new and distinct cultivar of *Begonia* plant, botanically known as *Begonia×hiemalis,* commercially known as Elatior Begonia and hereinafter referred to by the name 'Elektra White'.

The new *Begonia* is a naturally-occurring whole plant mutation of the *Begonia×hiemalis* cultivar Elektra Pink, disclosed in U.S. Plant Pat. No. 18,967. The new *Begonia* was discovered and selected by the Inventor as a flowering plant from within a population of plants of the parent cultivar in a controlled environment in Ermelo, The Netherlands or Jun. 9, 2004.

Asexual reproduction of the new *Begonia* by cuttings taken in a controlled environment in Ermelo, the Netherlands since November, 2004, has shown that the unique features of this new *Begonia* are stable and reproduced true to type in successive generations.

SUMMARY OF THE INVENTION

The cultivar Elektra White has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Elektra White'. These characteristics in combination distinguish 'Elektra White' as a new and distinct *Begonia:*

1. Upright and mounded plant habit.
2. Freely branching habit.
3. Double flowers that are white in color and held above and beyond the foliage.
4. Excellent postproduction longevity.

Plants of the new *Begonia* differ primarily from plants of the parent, the cultivar Elektra Pink, in flower color as plants of the cultivar Elektra Pink have dark pink-colored flowers.

Plants of the new *Begonia* can also be compared to plants of the cultivar White Netja, not patented. In side-by-side comparisons conducted in Ermelo, The Netherlands, plants of the new *Begonia* differed from plants of the cultivar White Netja in the following characteristics:

1. Plants of the new *Begonia* had narrower leaves than plants of the cultivar White Netja.
2. Flowers of plants of the new *Begonia* were more double than flowers of plants of the cultivar White Netja

BRIEF DESCRIPTION OF THE PHOTOGRAPHS

The accompanying colored photographs illustrate the overall appearance of the new *Begonia,* showing the colors as true as it is reasonably possible to obtain in colored reproductions of this type. Colors in the photographs may differ slightly from the color values cited in the detailed botanical description which accurately describe the colors of the new *Begonia.*

The photograph at the top of the sheet comprises a side perspective view of a typical flowering plant of 'Elektra White' grown in a container.

The photograph at the bottom of the sheet is a close up view of lower (left) and upper (right) surfaces of typical leaves and flowers of 'Elektra White'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in Ermelo, The Netherlands, under commercial practice in a glass-covered greenhouse during the spring and summer. Average day and night temperatures were about 20° C. during the first three to four weeks then lowered to an average day and night temperature of 18° C. until flowering. Four weeks after planting rooted cuttings in 12-cm containers, two five-day periods of long nyctoperiods of 16 hours were given and were separated by two days and subsequently followed by short nyctoperiods of eight hours until flowering. Plants were pinched one time about one week after planting. Plants were about twelve weeks from planting when the photographs and description were taken.

Botanical classification: *Begonia×hiemalis* cultivar Elektra White.

Commercial classification: Elatior Begonia.

Parentage: Naturally-occurring whole plant mutation of the *Begonia×hiemalis* cultivar Elektra Pink, disclosed in U.S. Plant Pat. No. 18,967.

Propagation:

*Type.*—By terminal vegetative cuttings.

*Time to develop roots.*—About 20 days at temperatures 20° C.

*Time to produce a rooted young plant.*—About six weeks at temperatures of 20° C.

*Root description.*—Fine, fibrous, well-branched; white/orange in color. Plants of the new *Begonia* have not been observed to form tubers.

Plant description:

*Plant form.*—Compact, upright and mounded plant habit, inverted triangle; freely branching with good stem and stem base strength. Flowers are double and abundant. Plants flower continuously.

*Growth habit.*—Vigorous growth habit; suitable for 9 to 14-cm containers. Under optimal environmental and cultural conditions, usually about 13 weeks are required to produce proportional 14-cm potted plants from cuttings. Vegetative shoots are formed at basal nodes and flowering shoots are formed at upper nodes.

*Plant height.*—About 22 cm to 27 cm.

*Plant width.*—About 45 cm.

*Leaves.*—Arrangement: Simple, alternate. Developing leaves, length: About 5 cm to 6 cm. Developing leaves, width: About 8 cm to 11 cm. Fully expanded leaves, length: About 10 cm to 13 cm. Fully expanded leaves, width: About 14 cm to 19 cm. Shape: Roughly reniform; oblique. Apex: Acute. Base: Cordate; oblique. Margin: Doubly serrate. Texture, upper surface: Smooth, glabrous; margins, slightly pubescent. Texture, lower surface: Smooth, glabrous. Venation pattern: Palmate. Color: Developing leaves, upper surface: Darker than 147A. Developing leaves, lower surface: 148B; color becoming closer to 148B with development. Fully expanded leaves, upper surface: Darker than 147A; venation, 146A to 146B. Fully expanded leaves, lower surface: 191A overlain with 178A; venation, 146B to 146C. Petiole length: About 2 cm to 7 cm. Petiole texture, upper and lower surfaces: Pubescent. Petiole color, upper and lower surfaces: Close to 146C to 146D.

Flower description:

*Flowering habit.*—Double flowers with numerous tepals arranged in axillary cymes. Usually eight to nine flowers per cyme. Many cymes in flower simultaneously. Flowers positioned above and beyond the foliage. Flowering continuous.

*Natural flowering season.*—Plants will flower year round regardless of nyctoperiod, however plants flower earlier and more abundantly from mid-February until November in the Northern Hemisphere.

*Flowers.*—Shape: Rounded; rose-like. Diameter: About 4 cm to 6 cm. Depth (height): About 1.5 cm to 2 cm.

*Flower buds.*—Length: About 1 cm to 16 cm. Diameter: About 0.8 cm to 1.6 cm. Color: Close to 145D.

*Tepals.*—Arrangement: Rosette. Quantity per flower: Usually about 10 to 25 per flower. Size: Outer tepals, length: About 2.8 cm to 3.5 cm. Outer tepals, width: About 2.8 cm to 4 cm. Inner tepals, length: About 1.2 cm to 2.3 cm. Inner tepals, width: About 1.4 cm to 2.3 cm. Shape: Rounded flabellate. Apex: Slightly retuse. Margin, outer and inner tepals: Entire. Texture, upper and lower surfaces: Smooth, glabrous; satiny. Color: When opening, upper and lower surfaces: Close to 157B. Fully opened, upper and lower surfaces: Close to 155D.

*Flower bracts.*—Quantity/arrangement: Two, opposite. Shape: Broadly cordate. Apex: Acute. Margin: Entire. Texture, upper and lower surfaces: Glabrous, smooth; at the margins, pubescence. Color, upper surface: Close to 146B. Color, lower surface: Close to 147C.

*Peduncles.*—Angle: Erect. Length: About 5 cm to 6 cm. Texture: Slightly pubescent. Color: Close to 144A.

*Pedicels.*—Angle: Erect. Length: About 1.2 cm to 3 cm. Texture: Slightly pubescent. Color: Close to 145A to 145B.

*Reproductive organs.*—Stamens: None observed. Pistils: None observed.

*Seed/fruit.*—Seed and fruit production have not been observed as reproductive organs are not formed.

Postproduction longevity:

*Individual flowers.*—Generally about two to three weeks.

*Whole plants.*—About eight weeks under interior conditions.

Disease/pest resistance: Resistance to pathogens and pests common to *Begonia* has not been observed.

Temperature tolerance: Plants of the new *Begonia* have been observed to tolerate temperatures from about 10° C. to about 35° C.

It is claimed:

1. A new and distinct *Begonia* plant named 'Elektra White' as illustrated and described.

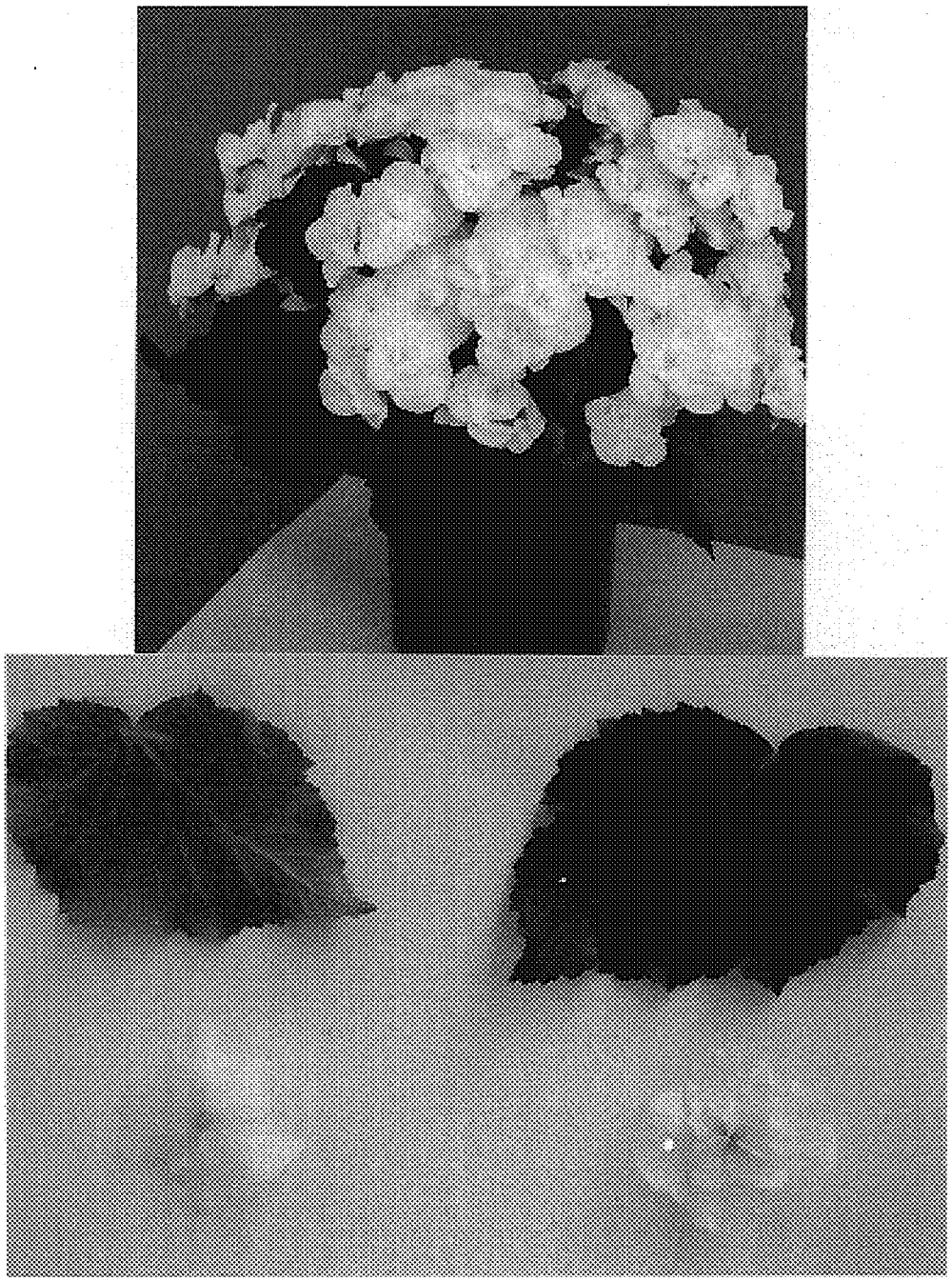

* * * * *